(12) United States Patent
Ell

(10) Patent No.: US 9,089,434 B2
(45) Date of Patent: Jul. 28, 2015

(54) LOW PROFILE KNEE IMPLANT

(71) Applicant: Phantom Orthopedics, LLC, Gresham, OR (US)

(72) Inventor: Shawn C. Ell, Gresham, OR (US)

(73) Assignee: Phantom Orthopedics, LLC, Gresham, OR (US)

( * ) Notice: Subject to any disclaimer, the term of this patent is extended or adjusted under 35 U.S.C. 154(b) by 77 days.

(21) Appl. No.: 13/842,497

(22) Filed: Mar. 15, 2013

(65) Prior Publication Data

US 2014/0277549 A1    Sep. 18, 2014

(51) Int. Cl.
*A61F 2/38* (2006.01)

(52) U.S. Cl.
CPC .................................... *A61F 2/3859* (2013.01)

(58) Field of Classification Search
CPC ......... A61F 2/38; A61F 2/389; A61F 2/3859; A61F 2220/0025
USPC ................... 623/20.14, 20.21–20.31, 20.35
See application file for complete search history.

(56) References Cited

U.S. PATENT DOCUMENTS

| | | |
|---|---|---|
| 4,215,439 A | 8/1980 | Gold et al. |
| 4,778,473 A | 10/1988 | Matthews et al. |
| 4,865,603 A | 9/1989 | Noiles |
| 4,964,868 A | 10/1990 | Bloebaum |
| 8,070,821 B2 | 12/2011 | Roger |
| 2008/0154270 A1* | 6/2008 | Haines et al. ................... 606/88 |
| 2009/0198340 A1* | 8/2009 | Cloutier et al. ............ 623/20.35 |

* cited by examiner

*Primary Examiner* — Jason-Dennis Stewart
(74) *Attorney, Agent, or Firm* — Schwabe, Williamson & Wyatt, P.C.

(57) ABSTRACT

A femoral implant for use as a component of an artificial knee having a thin, lightweight body with an articulating surface and an interior surface, the interior surface having one or more reinforcing members extending therefrom and extending across a substantial portion of said surface.

6 Claims, 5 Drawing Sheets

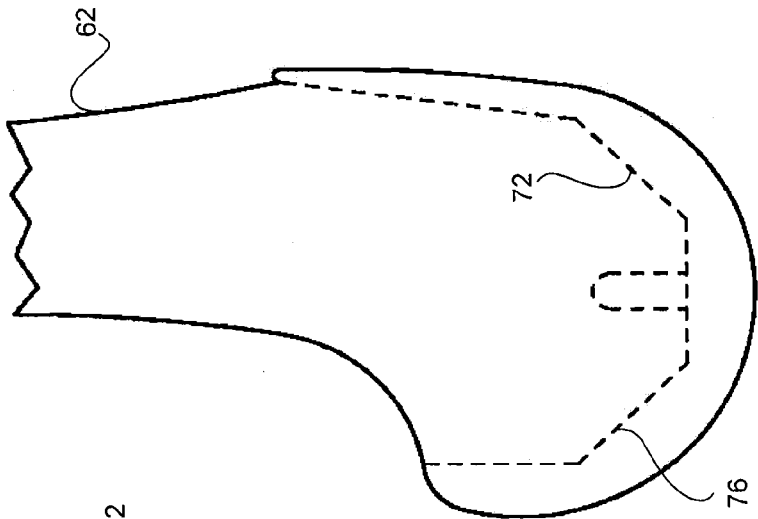
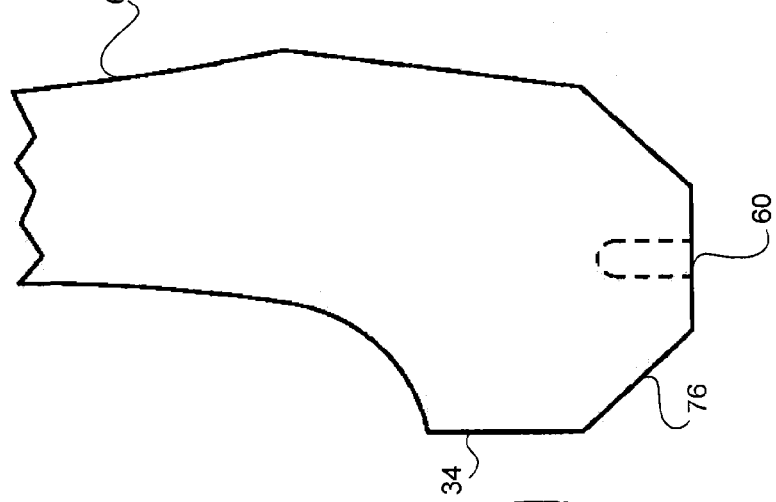
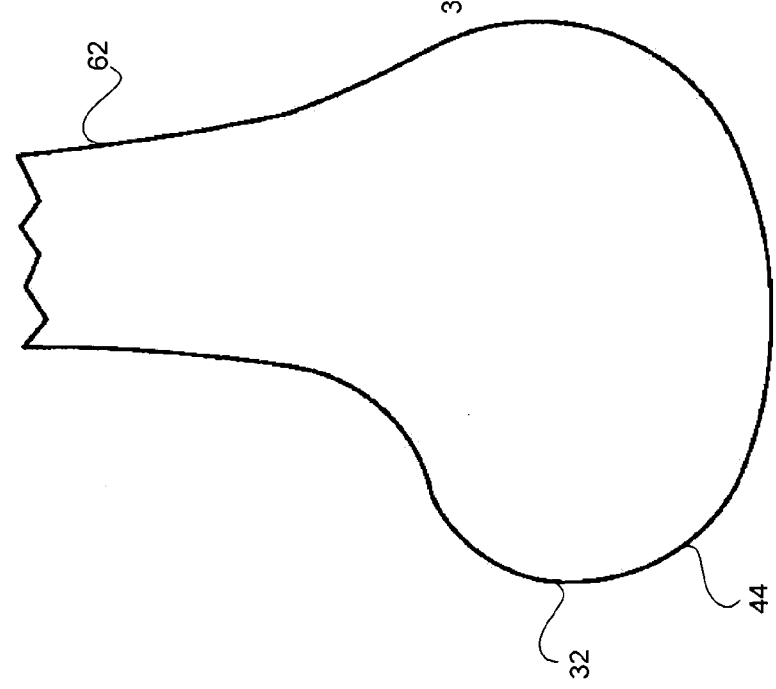

LOW PROFILE KNEE IMPLANT

BACKGROUND OF THE INVENTION

Nearly 400,000 total knee replacements are performed each year in the United States. This number is expected to grow to nearly 4 million by 2030. All knee replacements require removal of bone on both the tibia and femur. This is necessary in order to remove the damaged cartilage and bone as well as to accommodate the mass of the implant and provide for the proper spacing in the knee joint. The bone which is removed is replaced with a metallic, polymer, or ceramic implant.

Due to limitations in all known materials, the typical life of an implant is approximately 15 years. The lifespan of the implant is highly dependent on patient weight and physical activity. Failure of the implant causes significant pain, immobility, and possible infection. As the implant wears, small particles are released into the surrounding tissue which can cause irritation, possible infection, and loosening of the implant. When the implant fails, the patient must undergo a revision total knee surgery. A revision total knee surgery requires the removal of additional bone in order to properly affix the implant to the bones.

The need to remove bone in order to affix an implant limits the number of knee replacements a patient may receive. Typically after a patient has one revision knee replacement there is no longer a sufficient amount of bone to accommodate another revision surgery. Consequently, patients who need knee replacements must wait until their remaining lifespan is short enough to ensure that they do not outlive a single revision knee replacement. With a combined implant life of approximately 30 years, patients often either put up with the pain or significantly reduce their activity until they believe they have less than 30 years of remaining lifespan. This can have detrimental effects on their health, such as excessive weight gain and increased arthritis of the knee joint.

BRIEF DESCRIPTION OF THE DRAWINGS

FIG. 3*a* is a lateral view of a distal femur.

FIG. 3*b* is a lateral view of a distal femur which has been cut to receive a conventional implant.

FIG. 3*c* is a lateral view of a distal femur with attached conventional implant.

DETAILED DESCRIPTION

Disclosed herein are improved knee implants and methods for implanting them which require the removal of significantly less bone than a conventional implant. Removal of less bone means that a patient may receive an additional revision surgery, and need not put off knee replacement surgery for as long as is necessary using conventional technology.

Conventional knee replacement implants are generally solid in design. Knee replacements typically have a curved outer geometry which resembles the surface of the distal femur. The inner geometry typically contains 5 flat areas and two pins which are used to secure the implant to the distal femur. Knee implants have been manufactured from stainless steel, cobalt chrome, titanium, and zirconium. Conventional knee replacement implants are relatively thick, and as a consequence they require significant bone removal.

Figure 1:
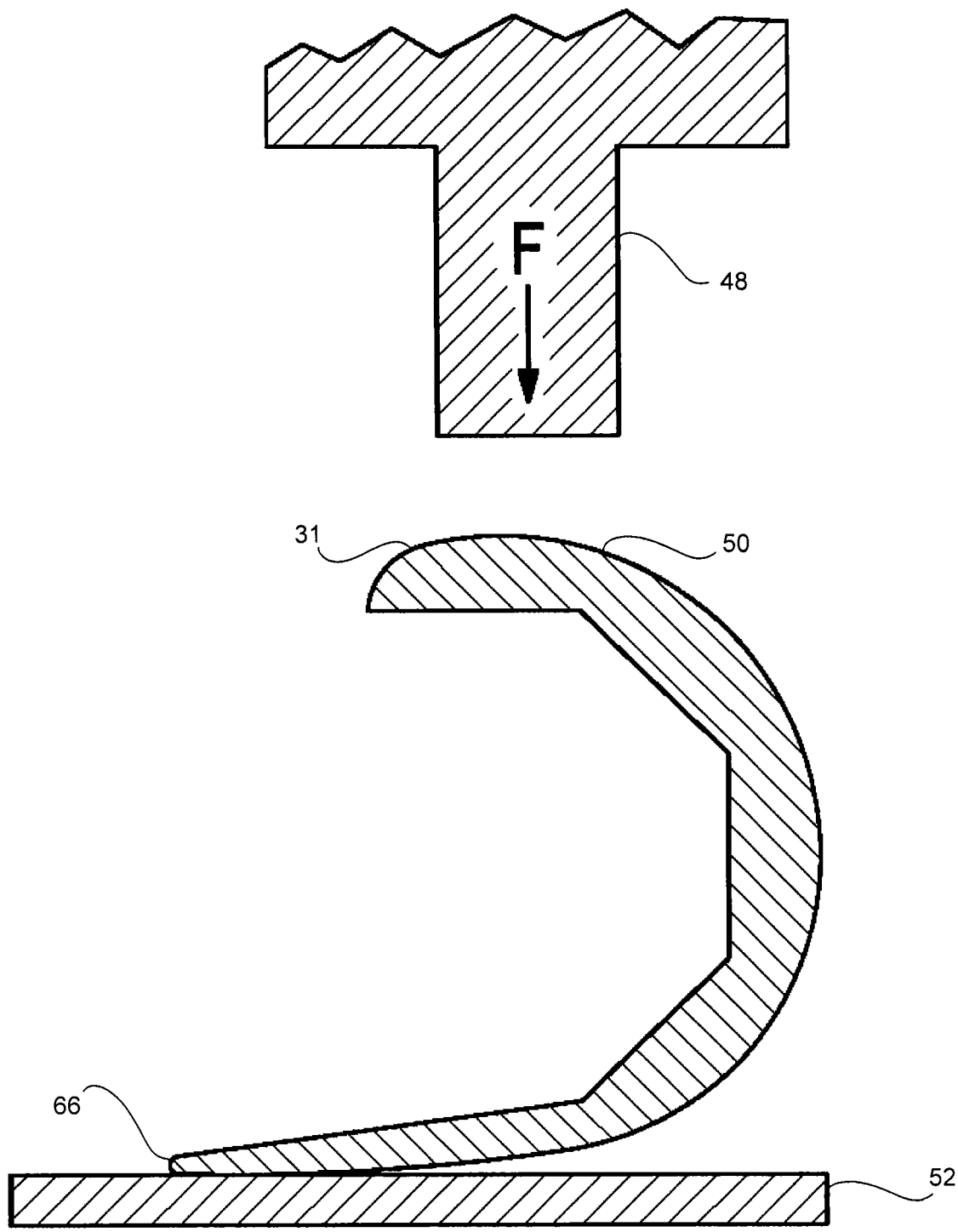
FIG. 1 is a schematic view of a knee implant undergoing a condyle test.

There is no FDA standard for fatigue strength testing of knee replacement implants. It is conventionally believed that the femoral implant for a total knee replacement must be subjected to a condyle test. As shown in FIG. 1, the condyle test is performed by applying a force with the impacting head of the testing apparatus 48 to the unsupported condyles 50 of the implant. This testing is conducted while the implant is fixed with the most anterior and proximal point 66 of the implant secured to the stage 52 of the testing apparatus while the testing apparatus exerts a force against the unsupported condyles 31 of the device. The design of implants has been driven by this testing methodology, as an implant needs significant thickness (on the order of 0.25 inches) in order to have enough strength to withstand the loads which the implant will be subjected to during testing.

Figure 2:
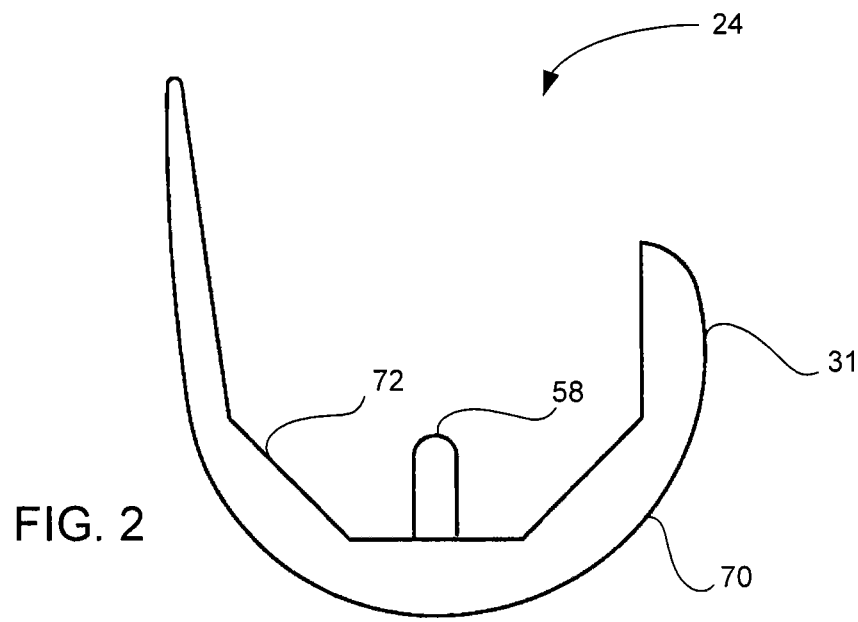
FIG. 2 is a lateral view of a conventional knee implant.

Conventional thinking in the field teaches away from the design of a thin implant because a thin implant will fail when subjected to the condyle test. Conventional implant 24, as shown in FIG. 2, have a thickness of approximately 0.25 inches and are solid. These implants have an articulating surface 70 which is curved. The geometry of the articulating surface is typically based on the average curvature measured in the distal femurs of numerous patients. Some implants may have an articulating surface 70 which is simply geometrically round. Either means of designing the curvature of the articulating surface 70 means that no implant fits a given patient perfectly. Implants typically have two posts 58 extending vertically from the interior surface 72 of the implant. These posts are used to secure the implant to a patient's femur, as the flat surfaces of a conventional implant do not provide much opportunity for a press fit method of fixation.

Implant design is also conventionally driven by the limitations in the complexity of cuts which can be made by surgeons removing bone by hand. Typically, all cuts to the articulating surface 44 of the femur 62 are made by hand by a surgeon using electrically powered cutting tools. These cuts are often made without the use of cutting guides. This limits the complexity of the cuts that can feasibly be made. Consequently, implant devices are conventionally relatively simple in order to accommodate the limitations of the surgeons implanting the devices.

Surgeons cutting by hand can only make flat surfaces, and so the interior surfaces 72 of conventional implants comprise flat planes 76. It is conventionally believed that interior surfaces 72 of implants must have planar surfaces 74 which can be affixed to the planar bone surfaces that physicians are capable of forming when using hand tools, as shown in FIGS. 3*a-c*. An uncut femur 32 has a fairly smooth curve from a lateral view, as shown in FIG. 3*a*. The traditional implant requires five flat cuts 76 to the femur 62, as shown in FIG. 3*b*, which remove a significant amount of bone. The flat areas on the interior surface 72 of the implant are then mated to the flat cut planes of the femur 62, as shown in FIG. 3*c*. Said implants also require that two holes 60 be drilled to accommodate the posts 58.

Implants designed to withstand conventional condyle testing and to be affixed to flat bone surfaces require the removal of a significant amount of bone. This removal of bone limits the number of revision surgeries that a patient can have.

The inventors of the devices and methods disclosed herein have realized that the condyle testing scenario does not realistically duplicate the loads the implant must sustain when it is in the human body. First, the inventors have observed that while in the body a knee implant is always supported by bone. Additionally, the distal portion of the implant 68, which is placed directly between the femur 62 and the tibia 12, not the condyles 10, will experience the greatest physiological load in vivo. The implant will encounter this load when the subject is impacting the ground with his or her knees locked, such as after a jump or when running. The loading scenario modeled by the condyle test only occurs when an individual moves to a standing position from a sitting position, in which event the load on the implant is typically less the patient's weight, as both legs will be used.

Because conventional condyle testing regimes do not realistically duplicate loads that implants feel when implanted into the body, they therefore do not accurately predict the risk that any given implant will fail in use. Moreover, modern surgical tools such as robots functioning as multi-axis milling tools can cut extremely complex shapes in bone with tremendous accuracy. Thus, the inventors have realized that the two premises driving the design of conventional implants: the requirements of the condyle test and limitations in surgical cutting techniques, are not necessarily valid.

The devices and methods disclosed herein can reduce bone removal resulting from a total knee replacement, and the inventive implants are lighter and more closely mimic the patient's natural knee geometry and motion.

Figure 4:
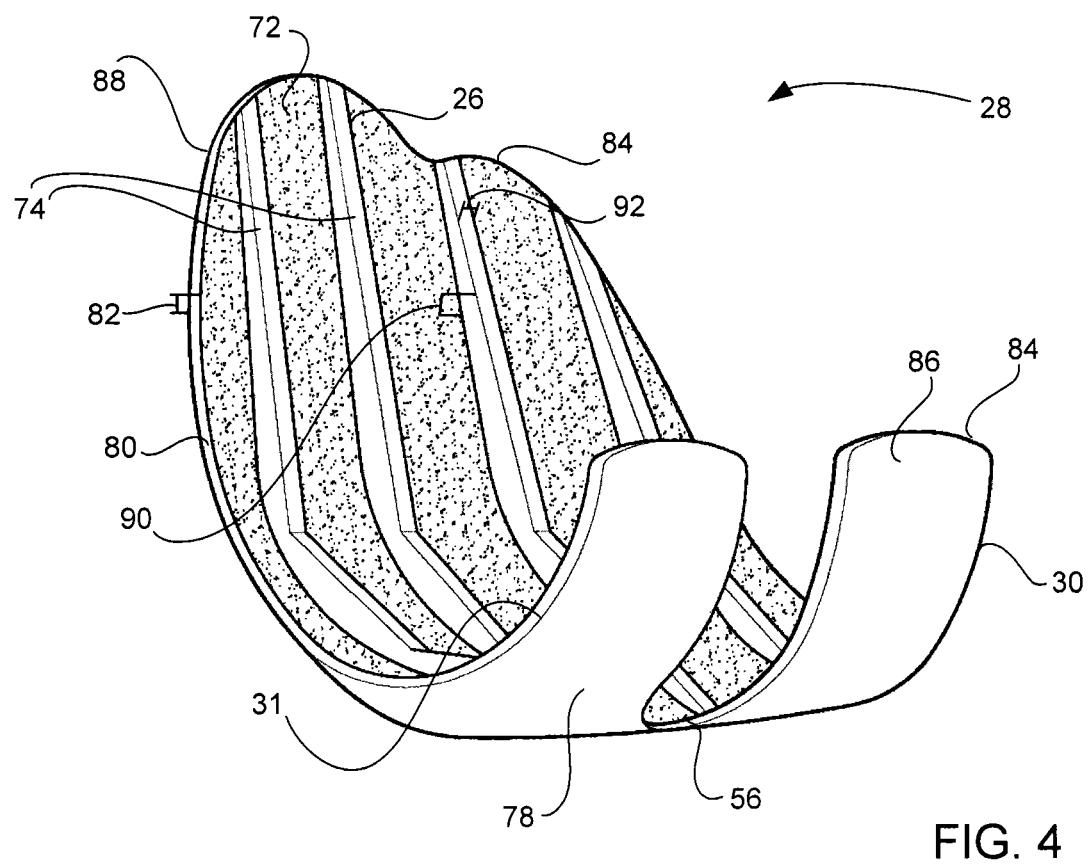
FIG. 4 is an isometric view of one embodiment of the inventive implant.

The inventive implants disclosed herein require the removal of much less bone, and utilize the capability of new surgical tools such as multi-axis milling capabilities of robots. As shown in FIG. 4, the implant comprises a body 80 with an interior 72 or proximal surface 74 which affixes to the femur 62 and which defines a cavity. The cavity may be transected by one or more additional reinforcing members 26. In an alternate embodiment, the inventive implant comprises a body 80 with a proximal surface which is transected by reinforcing members 26.

Figure 5:
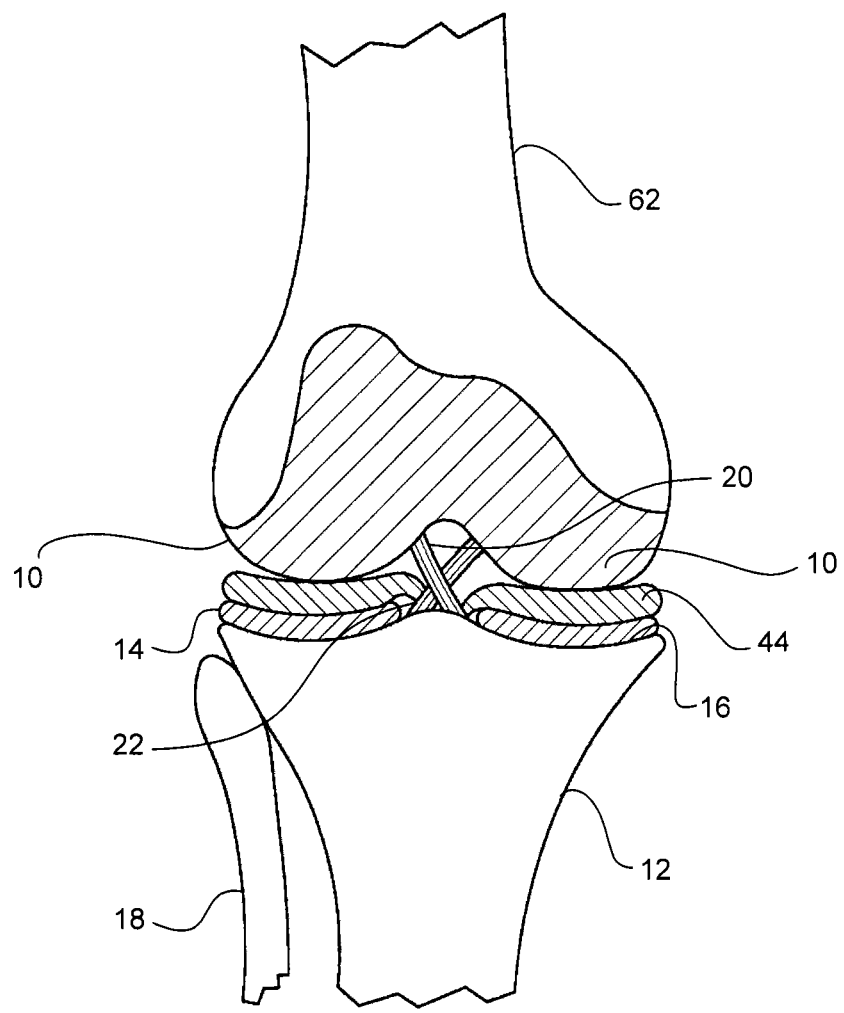
FIG. 5 is an anterior view of a knee joint.
Figure 6:
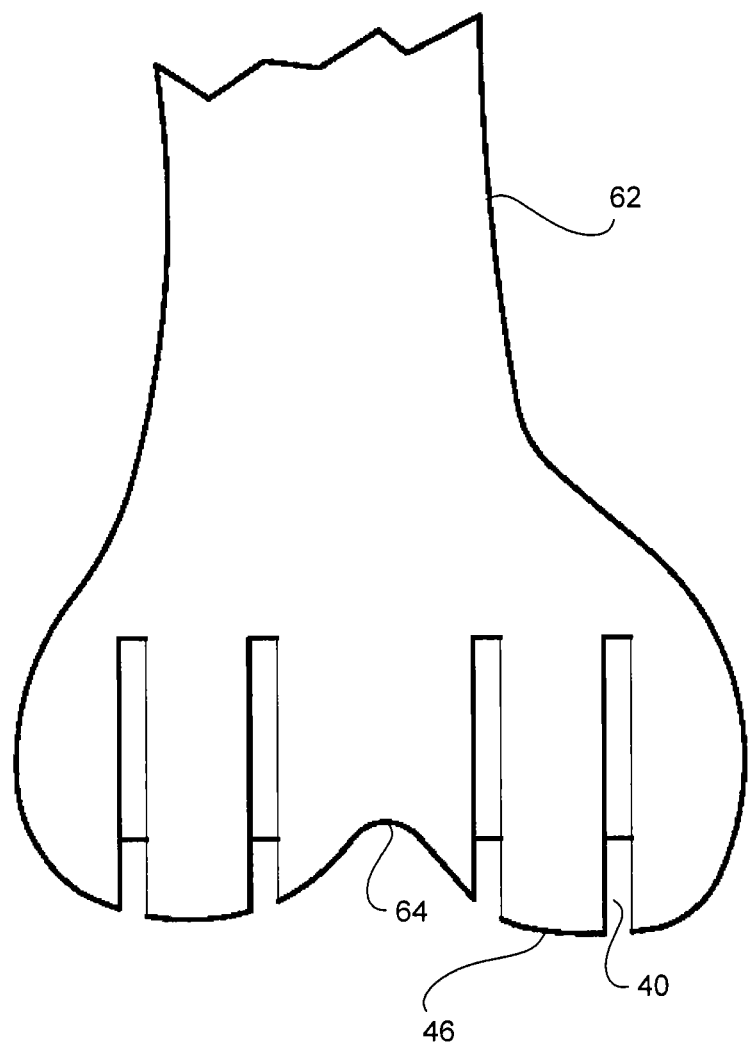
FIG. 6 is an anterior view of a distal femur which has been cut to receive one embodiment of the inventive implant.

The inventive implants are designed to replace the articular cartilage 44 of the femur 62. As shown in FIG. 5, cartilage covers the condyles 10 and articulating surfaces of the femur 44 which sit on the meniscus 14. During the operation the surgeon must detach the ACL 20 and PCL 22, which attach the femur to the tibia 12 and limit motion of the femur 62 relative to the tibia 12, in order gain proper access to the articulating surface 44 and cartilage 16 of the knee.

In one embodiment, the inventive implant 28 has body 80 which having two aspects, one of which forms an articulating surface 78 which mimics the articulating surface 44 of the patient's natural femur 62, and the other aspect defines an interior, proximal surface 72 which is affixed to the patient's distal femur.

An inventive implant may include a cut-out 56 in the implant where the intercondylar notch 64 is located. This is due to the fact that the condyles 10 of the femur 62 are the weight bearing surfaces, whereas the intercondylar notch 64 carries no load and need not be replaced.

The coverage of the inventive implant 28 mimics the coverage of the articulating cartilage 44 on the femur 62. The implant has a uniform thickness 82 in order to eliminate many possible stress concentrations which can be caused by a change in thickness. The inventive implant 28 may be manufactured out of a metallic or ceramic biocompatible material. The thickness 82 of the body 80 of the inventive implant may be between 1 mm and 5 mm thick.

The proximal or interior surface 72 of the inventive implant 28 contains one or more reinforcing members 26. These reinforcing members have a dual purpose; the first being to provide structural support to the implant, and the second being to provide a means to secure the implant 28 to the femur 62. The proximal surfaces 74 of these reinforcing members 26 can form a series of straight lines which roughly follow the curvature of the articular surface. As a result, straight cuts can be made in the distal femur to accommodate the reinforcing members.

Reinforcing members are preferably between 0 and 10 mm tall. The height of a single reinforcing member can vary as the member tapers toward the edges 84 of the implant. Reinforcing members can be spaced between 10 and 20 mm apart. Reinforcing members preferably extend longitudinally from the anterior aspect 86 of the implant to the posterior aspect 88 of the implant. The reinforcing members may all be the same height or they may be different heights.

In one embodiment, the inventive implant 28 may be secured using either of the traditional methods; press-fit or cementing of the implant.

Robots have begun to shift the paradigm in surgery. Currently robots have the capability of performing both total knee and total hip replacements. The use of a robot can increase the precision of a total knee replacement, leading to better alignment and greater overall satisfaction of the patient. These robots can also reduce surgery time.

Robots can be used to prepare a femur for the inventive implant. First a CT scan is taken of the joint which is to be replaced. The images are loaded into a program which turns the CT into a three dimensional file which can be altered using computer aided design software. This process allows the operator to select the proper implant and position is correctly on the bone. The program then writes a file which controls the motion of the robot. During surgery a surgeon guides the robot through the program as it machines the surface of the knee so that the implant fits perfectly.

A modern surgical robot is used to prepare the surface of the distal femur to receive the implant by removing a thin, uniform layer of bone from the articulating surface of the distal femur. The robot is then used to cut notches or grooves in the femur which are configured to receive the reinforcing members 26. The bone 46 between the notches 40 is preserved. The surgeon then fits the reinforcing members 26 into the notches 40 and secures the implant to the bone and closes up the wound.

Since the inventive implants require minimal bone removal, patients may be eligible to receive up to two revision surgeries. The first of the two revisions could consist of implanting the conventional implant 24. The second of the two revisions could involve implanting the current revision total knee implant. This means that patients may be able to receive their first knee replacement at a younger age.

If subjected to traditional condyle knee implant testing the inventive implants may fail. A more physiologically appropriate testing method would involve supporting internal surfaces of the implant with a material which mimics the properties of bone such as polymer foam like that made by Sawbones. Additionally the load should be applied in maximum extension of the joint as maximum stress on the knee joint occurs during the initial strike of the foot during a run. This same orientation occurs when landing from a jump. Less force should be exerted on the condyles. This testing methodology would better predict which implants are at risk of failing in use.

The terms and expressions which have been used in this specification are intended to describe the invention, not limit it. The scope of the invention is defined and limited only by the following claims.

What is claimed is:

1. A femoral implant for use as a component of an artificial knee, said implant defining an articular surface and an interior surface, said interior surface being configured to be affixable to a human distal femur, said interior surface having one or more reinforcing members protruding therefrom and extending across a substantial portion of said surface, each said one or more reinforcing members having two or more proximal surfaces which form a series of straight lines.

2. The implant of claim 1 wherein said one or more reinforcing members have at least one height, said height being less than 10 mm.

3. The implant of claim 1 wherein said one or more reinforcing members have proximal surfaces which define one or more flat planes.

4. The implant of claim 1 wherein said one or more reinforcing members have a height and a length, and said height varies over said length.

5. The implant of claim 1 wherein said implant is made from a ceramic material.

6. The implant of claim 1 wherein said body has a thickness, and said thickness is less than about 5 mm.

* * * * *